(12) United States Patent
Lum et al.

(10) Patent No.: US 8,435,273 B2
(45) Date of Patent: May 7, 2013

(54) HIGH POWERED LIGHT EMITTING DIODE PHOTOBIOLOGY DEVICE

(76) Inventors: Myk Wayne Lum, Irvine, CA (US); Frances A. Beckman, San Diego, CA (US)

( * ) Notice: Subject to any disclaimer, the term of this patent is extended or adjusted under 35 U.S.C. 154(b) by 36 days.

(21) Appl. No.: 13/186,679

(22) Filed: Jul. 20, 2011

(65) Prior Publication Data

US 2012/0022618 A1    Jan. 26, 2012

Related U.S. Application Data

(60) Provisional application No. 61/400,099, filed on Jul. 21, 2010.

(51) Int. Cl.
*A61N 5/06* (2006.01)

(52) U.S. Cl.
USPC ................................ 607/88; 607/87; 607/90

(58) Field of Classification Search ............... 607/88–94
See application file for complete search history.

(56) References Cited

U.S. PATENT DOCUMENTS

| | | | | |
|---|---|---|---|---|
| 6,019,482 A * | 2/2000 | Everett | .......................... | 362/184 |
| 7,810,963 B2 * | 10/2010 | Peck | ............................. | 362/346 |
| 7,896,908 B2 * | 3/2011 | Ripper et al. | ................... | 607/90 |
| 2003/0076281 A1 * | 4/2003 | Morgan et al. | .................. | 345/44 |
| 2007/0032847 A1 * | 2/2007 | Weckwerth et al. | ............ | 607/93 |
| 2007/0060984 A1 * | 3/2007 | Webb et al. | ..................... | 607/89 |
| 2009/0005839 A1 * | 1/2009 | Griffith et al. | .................. | 607/91 |
| 2009/0240310 A1 * | 9/2009 | Kennedy | ......................... | 607/89 |
| 2009/0310357 A1 * | 12/2009 | Huang | .......................... | 362/240 |

* cited by examiner

*Primary Examiner* — Bill Thomson
*Assistant Examiner* — Jeffrey Lipitz
(74) *Attorney, Agent, or Firm* — Henry M. (Chip) Bissell, IV (57) ABSTRACT

A high-powered light emitting diode (LED) photobiology (phototherapy) device is disclosed in the accompanying specification. The contemplated photobiology (phototherapy) device may be used in the treatment of various aesthetic and medical or other conditions. The phototherapy device may include a number of select LEDs for emitting a desired range or ranges of wavelengths of high intensity light for use in treatment. Additionally, the phototherapy treatment includes one or more methods for providing a treatment appropriate to the condition desired to be treated. The phototherapy device provides for a variety of high power light settings, intensity levels, and selectable time intervals for providing treatment.

8 Claims, 5 Drawing Sheets

SECTION A-A

HIGH POWERED LIGHT EMITTING DIODE PHOTOBIOLOGY DEVICE

CROSS-REFERENCE TO RELATED APPLICATION

This application claims the benefit of previously filed U.S. Provisional Application No. 61/400,099, filed with the U.S. PTO on Jul. 21, 2010.

BE IT KNOWN THAT WE, Myk Lum and Frances Beckman, each a citizen of the United States, have invented a new and useful high powered light emitting diode (LED) photobiology device of which the following is a specification:

BACKGROUND OF THE INVENTION

1. Field of the Invention

The present invention generally relates to apparatus and methods using light for phototherapy and more particularly, to photobiology devices incorporating high-power light-emitting diodes (LEDs) for use in human and/or animal phototherapy applications.

Phototherapy relates to the treatment of biological tissues using one or more ranges of light wavelengths. Such ranges may include visible, ultraviolet, and/or infrared light.

Compared with laser treatments and surgical procedures, the intensity of the light used in phototherapy is much lower and does not present the same level of risk as laser light. Common uses for phototherapy include wound healing, cellulite reduction, fat reduction, skin rejuvenation, pain relief, etc.

Phototherapy with light-emitting diode (LED) devices has been extensively studied in recent decades and has produced results demonstrating photo-biomodulation. Phototherapy treatments using high-powered LED devices of the type set forth herein take advantage of the bio-stimulatory effects of the light energy produced. Light energy is composed of photons (discrete packets of electromagnetic energy). The energy dose of light varies with the number of photons and their wavelength or color.

Photons delivered to living tissue may be scattered or absorbed. Scattered photons will be eventually absorbed by, or escape from, the subject tissue. Photons that escape the subject tissue do so through the action of diffuse reflection. Absorbed photons may interact with one or more organic molecules and/or chromosphores within the subject tissue. These interactions with the subject tissue produce photochemistry. Appropriate controlled application of light is capable of producing beneficial results.

The underlying object of the invention is the providing of an apparatus for use in phototherapy of the skin and body to achieve improved cosmetic, medical, and psychological results. The device of the present invention incorporates a selected range and/or combination of light sources, wavelengths, frequencies (hertz) and photon dosages to achieve optimal photo-biological benefits while provided in a variety of user-friendly configurations to allow for a range of professional and consumer applications.

2. Description of the Related Art

This invention pertains to the field of Phototherapy and phototherapeutic applications. Phototherapy consists of exposure to specific wavelengths of light using light-emitting diodes (LEDs) (as individual LEDs and/or arrays of LEDs) as light sources, for a prescribed amount of time to treat disease, provide symptomatic relief and affect cosmetic enhancements to hair, skin and body.

The use of phototherapy in medical science and aesthetic applications is rapidly evolving and increasing. More and more benefits are being revealed for applying selected wavelengths of light to various sections of tissue in order to stimulate cellular proficiency and enhance the body's ability to heal and rejuvenate itself. Phototherapy is finding beneficial applications in the treatment of acne, wrinkles, sun and age spots, rosacea, eczema, hair loss, and wound healing, symptomatic pain relief, and physical medicine rehabilitation.

As set forth above, phototherapy can provide multiple benefits. Beneficial ranges of light wavelengths may overlap each other in treating certain ailments and work to promote a variety of benefits to the hair, skin, and body. These light sources are often used in combinations to provide increase efficacy and various degrees of stimulation.

Throughout the years, science has determined the effects of various ranges of wavelengths of light, but absorption has proven to be the key to cellular change. Phototherapy emits photons that are absorbed by photoreceptors in the skin and body. All cells are photo-receptive and can be stimulated at differing depths dependent upon wavelength. Hair and skin cells respond well to phototherapy involving low level light due to the fact that cells reside just underneath the skin surface, making these low levels of energy able to reach the receptor sites and induce desired photochemistry to achieve beneficial results.

There are a number of phototherapy devices currently available for home or professional use to treat skin, body, and hair. These existing devices suffer from a number of deficiencies. The professional units are often stationary and rather large and cumbersome. This is primarily a result of the large number of LEDs necessary to achieve the desired light intensity. Similarly, consumer or personal devices are commonly underpowered due to the inability to provide an adequate number of LEDs in a handheld or otherwise conveniently sized unit. Such existing handheld units are lacking in both the ability to deliver adequate light intensity and the selectability of an adequate range of wavelengths to achieve desired results. Furthermore, existing phototherapy devices generally do not allow multiple wavelengths to be operated simultaneously, nor have integrated optics. Integrated optics are important as they enhance light intensity due to reduced dissipation, allow a user to control the area and size of treatment, and are less of a health contamination issue as the device does not touch the skin.

Prior art LED phototherapy devices have been less effective and even ineffective, because of incorrect emission wavelengths. In addition, prior art devices have produced LED power output that is insufficient to sustain beneficial effects of phototherapy. Other previous phototherapy devices may have sufficient LED power output but are large and very expensive, eliminating their potential use in personal medical and aesthetic care, requiring instead costly trips to a professional's office.

U.S. Pat. No. 7,513,906 (Passy, et al.) describes a phototherapy apparatus incorporating interconnected radiation sources for providing irradiation over time to aid in bone healing, growth, and regeneration. Like many similar devices, the apparatus of Passy, et al. suffers from the use of excessive numbers of diodes while limiting the convenience and versatility of the apparatus resulting from a limited range of light energy wavelengths.

U.S. Pat. No. 6,019,482 (Everett) describes a hand-held, self-contained irradiator powered by batteries. The irradiator provides an applicator having many diodes that emit electromagnetic radiation in the visible and/or infrared portions of the spectrum. Switches are provided for a user to activate to provide particular wavelengths or to be emitted from the applicator end to treat particular body surface areas for the relief of pain or other problems. This irradiator fails to deliver light energy levels adequate for the desired benefits and in effort to generate adequate light, incorporates an excessively large array of diodes that creates heat issues and significantly reduces convenience of use and effectiveness.

U.S. Pat. No. 7,686,839 (Parker) describes phototherapy treatment devices for applying close proximity area lighting to a wound for applying light/heat energy to aid in healing but does not provide the convenience and flexibility of use needed to provide a versatile and user-friendly device.

U.S. Pat. No. 7,198,634 (Harth, et al.) teaches the advantages of phototherapy for inducing the nitric oxide (NO) effect of dilating vascular walls, but does so within a limited infrared light source in combination with topical ingredients, reducing the over-all effectiveness of such a procedure. The apparatus of the present invention does not rely on the use of topical ingredients for photoactivation, but rather is capable of providing beneficial treatments without such adjuncts.

SUMMARY OF THE INVENTION

In view of the foregoing disadvantages inherent in the known types of phototherapy devices now present in the prior art, the present invention provides a new phototherapy (photobiology) device having high-powered light emitting diodes providing adjustable optical power output at predetermined wavelengths and associated methods for the beneficial application thereof.

Each year, people spend countless millions of dollars for skin-care products, symptomatic pain relief and medical treatments. The market for such products and treatments is growing and becoming more and more important. Some products and treatments have been developed around phototherapy, which uses light of selected wavelengths to help repair damaged skin, improve health, alleviate pain, and accelerate the healing process.

The present invention discloses a device and associated methods for improved healing, symptomatic pain relief, physical medicine/rehabilitation, and anti-aging procedures for treatments of an individual. Such treatments may be applied by professional or by consumers themselves as preferred.

In the presence of predetermined ranges of light wavelengths, wound healing and other beneficial processes contributing to anti-aging and relief from a variety of maladies may be achieved in manner and effectiveness unmatched by prior art devices.

A range of light frequencies is indicated by various colors (i.e., wavelengths) of the spectrum. By utilizing various wavelengths, colors relatively close on the spectrum can cause different effects when applied to various portion of the body.

Certain wavelengths of light at certain intensities have been found to aid tissue regeneration, resolve inflammation, relieve pain, and boost the immune system. The exact mechanism is the subject of ongoing investigation, but it is generally accepted that the principle mechanism is photochemical as opposed to heat-related. Observed biological and physiological effects include changes in cell membrane permeability, and up-regulation and down-regulation of adenosine triphosphate (ATP) and nitric oxide (NO).

In one example, red light from a 1-10 watt high power LED, at approximately 670 nanometers, is used to prevent hair loss and re-grow new hair, as well as to cause increased melanin production and protein synthesis. (All light wavelengths or ranges of wavelengths specified herein represent a general reference area of energy) Although the mechanism of action is not yet fully understood, it is believed that the beneficial effects set forth herein are derived from a relatively small band of light wavelengths extending on either side of the referenced wavelengths. For this reason, all light wavelengths or ranges of wavelengths herein are deemed to indicate a wavelength value having a range of plus or minus five nanometers (+/−5 nm).

Red, infrared, and near infrared light have also been used to increase collagen production and to reduce redness, dilated capillaries, and damage to the skin, as well as the reduction of fine wrinkles. They also provide symptomatic pain relief and stimulate wound healing.

Blue light has been found to reduce acne and when combined with red light, eliminates acne and reduces the scarring often associated with acne treatments.

Yellow and amber lights have been found to reduce fine lines, wrinkles, rosacea, eczema, and can help to repair sun-damaged skin.

Green light has been shown to reduce and eliminate sun and age spots, Seasonal Affective Disorder (SAD) and other psychological disorders, lighten freckles and also help promote more luminous skin condition and overall radiance of the skin.

All wavelengths of light have the ability to photo-stimulate the neuro/musculo-skeletal system and acupuncture/trigger points.

The general purpose of the present invention, which will be described subsequently in greater detail, is to provide an innovative high-powered light-emitting diode (LED) photobiology device that has many of the advantages of the larger, professional phototherapy devices mentioned heretofore, and many novel features that result in a new photobiology (phototherapy) device having high-powered light-emitting diodes (LEDs) for generating selected wavelength combinations, which is not anticipated, rendered obvious, suggested, or even implied by any of the prior art phototherapy devices, either alone or in any combination thereof. Novel and nonobvious methods for practicing the described applications of the device are described.

To attain this, the present invention generally comprises a housing for protecting and arranging the components; a power source and appropriate converter that allows for use of either AC or DC power; a cooling means for providing necessary cooling of device components; heat sink means for effective heat transfer; controls necessary to enable user-selective on/off operation, LED/wavelength operation and/or combination, and device reset; a timing circuit to allow user-selected dosage periods of from generally 1 to 5 minutes; a light emitter portion housing a plurality of select LEDs, including but not limited to: a blue LED and associated optic providing emission at or around 415 nm (nanometers); a green LED and associated optics providing emissions at or around 525 nm; an amber LED and associated optics providing emissions at or around 590 nm; a deep red LED without optics or a deep red LED with associated optics providing emission at or around 660 nm; and an infrared LED with associated optics providing emission at or around 850 nm.

Generally speaking, the wattage ratings for such LEDs must be greater than 1 watt in order to provide a desired level of treatment effectiveness. Power levels of 1 watt or less are insufficient to enable therapeutic noncontact use of a hand-held photobiology device. However, applicant has applied increased wattage levels of up to 10 watts in the development of devices for treatment. By surpassing the accepted limits of prior art devices applicant has discovered that such wattage levels enable both contact and noncontact therapeutic treatments to be realized. In accordance with applicant's findings, and to avoid potentially undesirable effects and possible tissue damage, LED power levels should not exceed 10 watts.

The light emitter portion of the device may include a combination of discrete LED devices. Such LED devices are selected and arranged to radiate light over a selected range of specific wavelengths or combinations of selected ranges of wavelengths. The LED devices and associated electronic controls and circuitry are arranged in a housing for protection and convenient use.

The device of the present invention provides a combination of high power light-emitting diodes having specific optical output at predetermined wavelengths. Special optics, adapted to such wavelengths are provided to achieve desired direction and distribution of energy. Such optics, also known as lenses or collimators, are specially designed to enable the intense light of a LED to be diffused or spread evenly across a broader emitting surface. Thereby allowing the beneficial light to be directed evenly across a larger treatment area. This greatly reduces the need for multiply redundant arrays of LEDs and provides greater efficiency and reduced heat generation.

In traditional phototherapy devices, LEDs experience significant loss of power at distance. It is not uncommon for prior art devices to lose more than 50% of their emitted power at a distance of just ½". In marked contrast, the present invention incorporates high-power LEDs with reflector optics having dispersion angles of approximately 45-90 degrees. The unprecedented combination of high-power LEDs with such optics enables the present invention to deliver the desired light output with uniform intensity diffused across a large area. This allows the device to be used for either contact or non-contact methods of treatment.

The present invention seeks to address the limitations and shortcomings of presently known phototherapy treatment devices. Prior art devices have required skin contact with the phototherapy device in order to deliver the desired treatment. Such contact has attendant risks associated with bacteria transfer, contamination, and patient discomfort when treating sensitive or difficult to reach areas.

The device of the present invention does away with the prior art limitation of direct contact by employing specially designed reflector optics and high-power LEDs having predetermined frequency outputs. This unique combination allows for novel, non-contact therapeutic use of the phototherapy device set forth herein. Such non-contact treatment overcomes significant obstacles faced by prior art devices with respect to treating sensitive, painful, or difficult to reach areas of the body.

By incorporating the optics' emitting surface into the surface of the housing, the present invention provides a device that can be quickly and easily cleaned and sterilized between uses.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings.

The invention is capable of other embodiments and of being practiced and carried out in various ways. Also, it is to be understood that the phraseology and terminology employed herein are for the purpose of the description and should not be regarded as limiting.

A primary object of the present invention is to provide a high-powered light-emitting diode photobiology device having human/animal application that overcomes the identified shortcoming of the prior art devices.

An object of the present invention is to provide a high-powered LED photobiology device having a sealed light-emitting surface for enabling cleaning and sterilization of the devices prior to use.

Another object of the present invention is to provide a high-powered LED photobiology device having optics associated with LEDs for controlling diffusion and intensity of emitted light over a larger area to improve treatment efficacy.

Another object of the present invention is to provide a high-powered LED photobiology device having selected combinations of predetermined light frequencies for use over a range of treatment durations.

Another object of the present invention is to provide a high-powered light-emitting diode photobiology device for treatment of, and applications including, tissue repair, wound healing, and prevention of tissue death.

Another object is to provide a high-powered light-emitting diode photobiology device for treatment of, and applications including, relief of inflammation, pain, edema, and acute and chronic diseases.

Another object is to provide a high-powered light-emitting diode photobiology device for treatment of, and applications including, neurogenic pain, neurological problems including neuronal toxicity, nerve regeneration, and stimulation.

Another object is to provide a high-powered light-emitting diode photobiology device for treatment of, and applications including, traditional Chinese medicine—colorpuncture, stimulation of acupuncture/trigger points (1-40 mm), and Bonghan channel hyaluronic acid/stem cells.

Another object is to provide a high-powered light-emitting diode photobiology device for treatment of, and applications including, behavioral healthcare/psychiatric treatment including Seasonal Affective Disorder (SAD), depression, anxiety, Post-Traumatic Stress Disorder (PTSD), addiction, pain and sleep disorders. Device treatment can be used in conjunction with traditional therapeutic modalities, e.g. cognitive-behavioral, biofeedback, EMDR, deep relaxation, etc.

Another object is to provide a high-powered light-emitting diode photobiology device for treatment of, and applications including, musculoskeletal system (muscles, ligaments, tendons, joints, bones) repair, improved strength and flexibility.

Another object is to provide a high-powered light-emitting diode photobiology device for treatment of, and applications including, syntonic optometry (although direct viewing of light is not recommended).

Another object is to provide a high-powered light-emitting diode photobiology device for treatment of, and applications including, non-invasive trans-cranial therapies.

Another object is to provide a high-powered light-emitting diode photobiology device for treatment of, and applications including, aesthetics, allergology, athletic training, cardiology, dentistry, dermatology, disaster medicine, endocrinology, gastroenterology, general medicine, gerontology/geriatrics, gynecology, hematology, immunology, infectious disease, military medicine, neurology, obstetrics, oncology, ophthalmology, palliative medicine, psychiatry/behavioral healthcare, pulmonology, radiology, rehabilitation medicine, rheumatology, sexual health, sleep medicine, sports medicine, surgery, toxicology, urology, veterinary medicine, traditional Chinese medicine, and syntonics.

Yet another object is to provide one or more methods for use of a high-powered LED photobiology device or devices for treatment in association with aesthetics, athletic training, cardiology, dentistry, dermatology, disaster medicine, endocrinology, gastroenterology, general medicine, gerontology/geriatrics, gynecology, hematology, immunology, infectious disease, military medicine, neurology, obstetrics, oncology, ophthalmology, palliative medicine, psychiatry/behavioral healthcare, pulmonology, radiology, rehabilitation medicine, rheumatology, sexual health, sleep medicine, sports medicine, surgery, toxicology, urology, veterinary medicine, traditional Chinese medicine, and syntonics.

Another object is to provide one or more methods for use of a high-powered LED photobiology device or devices for treatment in association with non-invasive trans-cranial therapies.

Another object is to provide one or more methods for use of a high-powered LED photobiology device or devices for treatment in association with syntonic optometry.

Another object is to provide one or more methods for use of a high-powered LED photobiology device or devices for treatment of the musculoskeletal system (muscles, ligaments, tendons, joints, bones) for repair, improved strength and flexibility.

Another object is to provide one or more methods for use of a high-powered LED photobiology device or devices for treatment in association with behavioral healthcare and/or psychiatric treatment including but not limited to Seasonal Affective Disorder (SAD), depression, anxiety, Post-Traumatic Stress Disorder (PTSD), addiction, pain and sleep disorders.

Another object is to provide one or more methods for use of a high-powered LED photobiology device or devices for treatment in association with traditional therapeutic modalities, e.g. cognitive-behavioral, biofeedback, EMDR, or deep relaxation.

Another object is to provide one or more methods for use of a high-powered LED photobiology device or devices for treatment in association with traditional Chinese medicine including but not limited to color-puncture, stimulation of acupuncture/trigger points (1-40 mm), and Bonghan channel hyaluronic acid/stem cells.

Another object is to provide one or more methods for use of a high-powered LED photobiology device or devices for treatment of neurogenic pain, neurological problems including but not limited to neuronal toxicity, nerve regeneration, and stimulation.

Another object is to provide one or more methods for use of a high-powered LED photobiology device or devices for treatment of inflammation, pain, edema, and acute and chronic diseases.

Syntonics, sometimes referred to as optometric phototherapy, describes a branch of ocular science that deals with the application of select light frequencies (or wavelengths) to the eyes. It has been in clinical optometric use for decades and proven successful in treating a variety of visual dysfunctions including lazy eye and problems with focusing and convergence.

Light is essential to life. Our planet revolves around a light source, the sun, and life on earth is dependent upon sunlight. Certain biochemical conditions in the brain need to be present in order for effective cortical plasticity and advanced functions to take place. A variety of neurotransmitters are fundamental to this biochemistry and allow for additional synoptic connections to initiate movement and further growth. The application of a select range of wavelengths as high-powered light can provide powerful and effective therapy to stimulate the brain's biochemistry.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only and that changes may be made in the specific construction illustrated.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENTS

The device of the present invention provides a combination of high-powered light-emitting diodes (LEDs) each having specific properties of optical output power at specific wavelengths of emission. The LEDs are equipped with specific integrated optics adapted to the LED's respective wavelengths.

In marked contrast to the use of lasers for phototherapy, the LEDs of the present invention generate noncoherent, or out-of-phase, light—wherein the light waves are not synchronized. This provides the beneficial result of LEDs being a safe, diffused light source that does not burn or damage tissue as can laser light.

Unlike traditional lasers phototherapy devices and methods, this present invention uses an innovative and novel combination of continuous high-powered LEDs, having specific optical output power(s) at specific wavelengths. The LED devices of the present invention also incorporate specified optics developed to enhance the efficacy of their respective wavelengths. The result is a range of phototherapy devices and methods for using such phototherapy devices that provide a safe diffused light source in contrast to the burning or similar damage that can occur with use of a laser.

Reference is now made to the accompanying drawing sheets and their figures. From figure to figure, like reference numerals refer to and correspond with like elements. Even though the drawing sheets and figures present various aspects of the embodiments depicted, the figures are not necessarily drawn to scale.

Persons skilled in the art will recognize that the systems and methods disclosed herein may be practiced without one or more of the specific details, or with other methods, components, materials, etc. In some instances, well-known structures, materials, or operations are not shown or described in detail. The described features, structures, or characteristics may be combined in any suitable manner in one or more embodiments. It is also readily understood that components of the embodiments, as generally described and illustrated in the figures herein, could be arranged and designed in a wide variety of different configurations.

For this application, the phrases "connected to" and "coupled to" are used to refer to any form of interaction between two or more entities, including mechanical, electrical, magnetic, electromagnetic, fluid, and thermal interaction. Two components may be coupled to each other even though they are not in direct contact with each other.

Turning now descriptively to the drawings, in which similar reference characters denote similar elements throughout the several views, the accompanying figures illustrate a high-powered light emitting diode (LED) photobiology device in accordance with the present invention.

Figure 1:
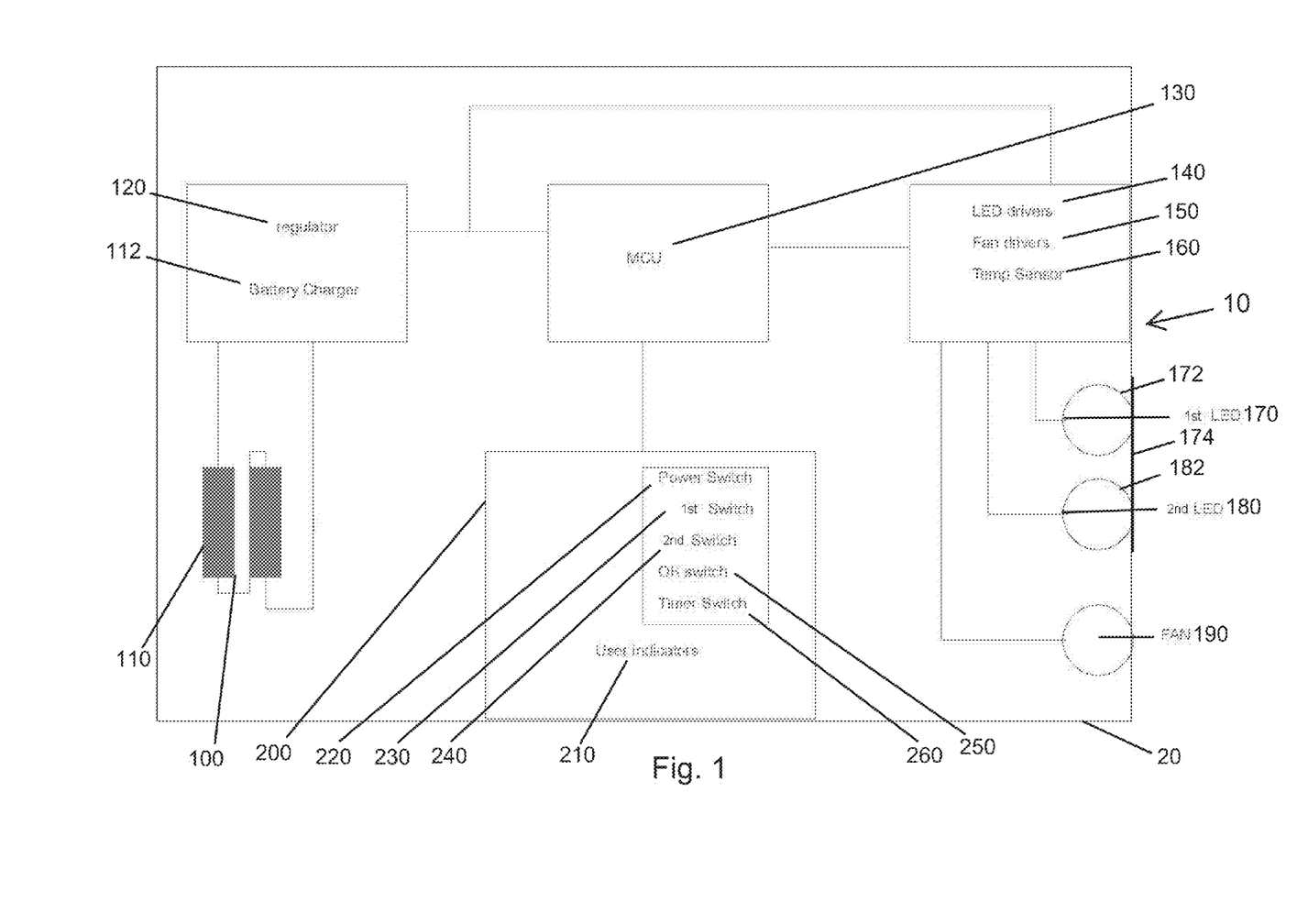
FIG. 1 is a block diagram of a representative control circuit for one embodiment of the present invention.

Referring now to FIG. 1, an embodiment of a high-powered light emitting diode (LED) photobiology device 10 in accordance with the present invention includes a housing 20 adapted to at least partially surrounds the components in order to provide necessary protection and facilitate handling and manipulation by a user. First optic 172 and second option 182 may be preferably integral to housing 20 to facilitate construction but not necessarily so. Such optics as 172 and 182 are preferably arranged to deliver 45-degree output angle of dispersion. Output angles for suitable optics can range from 45-90 degrees. One example of such optics is part no: RGB-1WS-LM45, Lens and Mount Assembly, available from Super Bright LEDs Inc, at www.superbrightleds.com. Such optics feature up to 90% efficiency and are suitable for devices in accordance with the present invention. The performance achieved through the use of optics is beneficially improved through a combination of reflective and diffusive surfaces to provide the desired output angle of dispersion and even distribution of light output across the output face.

By integrating the necessary optics in the construction of the device, optics 172 and 182 may combine with housing 20 to provide a sealed surface enabling ease of cleaning and sterilization. LEDs 170 and 180 are positioned with respect to optics 172 and 182, respectively, to provide the spatial radiation pattern desired for a chosen treatment. The degree of angular displacement of light intensity produced by LED 170 or 180 is relative to the distance at which the device may be held with respect to the area to be treated. Optionally, diffuser 174 is preferably employed to achieve greater uniformity of the dispersed light energy. Diffuser 174 consists of a translucent or frosted layer of suitable material, often plastic or glass. Diffuser 174 is preferably integral with housing 20, or may be incorporated into the construction of reflectors 172 and 182.

LEDs 170 and 180 can be selected to generate light of different frequencies. Different selected light frequencies produce different muscle contraction frequencies. By combining LEDs 170 and 180, the device of the present invention creates a frequency interference pattern of muscle contraction frequencies. This interference pattern produces stimulation similar to electrical muscle stimulation products without the need for direct electrical contact with the patient.

The incorporation of near-infrared or infrared frequencies enable the device of the present invention to achieve treatment with levels of energy penetration in marked contract to prior art devices.

Power supply 100 is connected to micro-controller unit (MCU) 130 to enable powering of apparatus. Optionally, power supply 100 may be connected to battery charger 112, battery 110, and regulator 120 to enable the device to be used while free from an AC power cord connection.

Micro-Controller Unit (MCU) 130 is connected to power supply 100 of choice, and LED drivers 140, fan drivers 150 and temperature sensor 160, each of which is also connected to power supply 100 as necessary. MCU 130 receives signals from LED drivers 140, fan drivers 150 and temperature sensor 160 and, in accordance with software code programming well known in the art, delivers controlling signals to LED drivers 140 to provide the light output desired. Similarly, MCU 130 delivers controlling signals to fan drivers 150, at least partially in response to signals received from temperature sensor 160, to operate fan 190 in order to prevent components of the apparatus of the present invention from overheating.

LED drivers 140 are each associated with one or more of first LED 170 and second LED 80. Additionally LEDs, not shown, are contemplated as being within the scope and breadth of the present invention. Said first LED 170 and second LED 180 are positioned in relation to first optic 172 and second optic 182 in order to utilize said optics to apply the desired light wavelengths in a preferred direction for application.

Apparatus 10 further incorporates a user control 200, said user control 200 providing a location, either upon or incorporated in said housing 20, for user indicators 210. Said user indicators 210 are connected to MCU 130 as is known in the art to establish a variety of means for enabling a user to interact with the apparatus 10, including operating the device and ascertaining the status and condition of the device relative to use. Such user indicators 210 include a power switch 220, a first switch 230 and a second switch 240. Said first switch 230 and seconds switch 240 are connected to MCU 130 and with LED drivers 140 to allow a user to indicate and obtain the pattern of LED light desired. Additional switches, not shown, are contemplated as being within the scope and breadth of the invention herein.

An "OK" switch 250 and a timer switch 260 are also in connected to MCU 130. Said OK switch enables a user to register approval for selected settings of apparatus controls and features. Said timer switch 260 enables a user to select a desired duration of high-powered light generation.

Figures 2, 3:
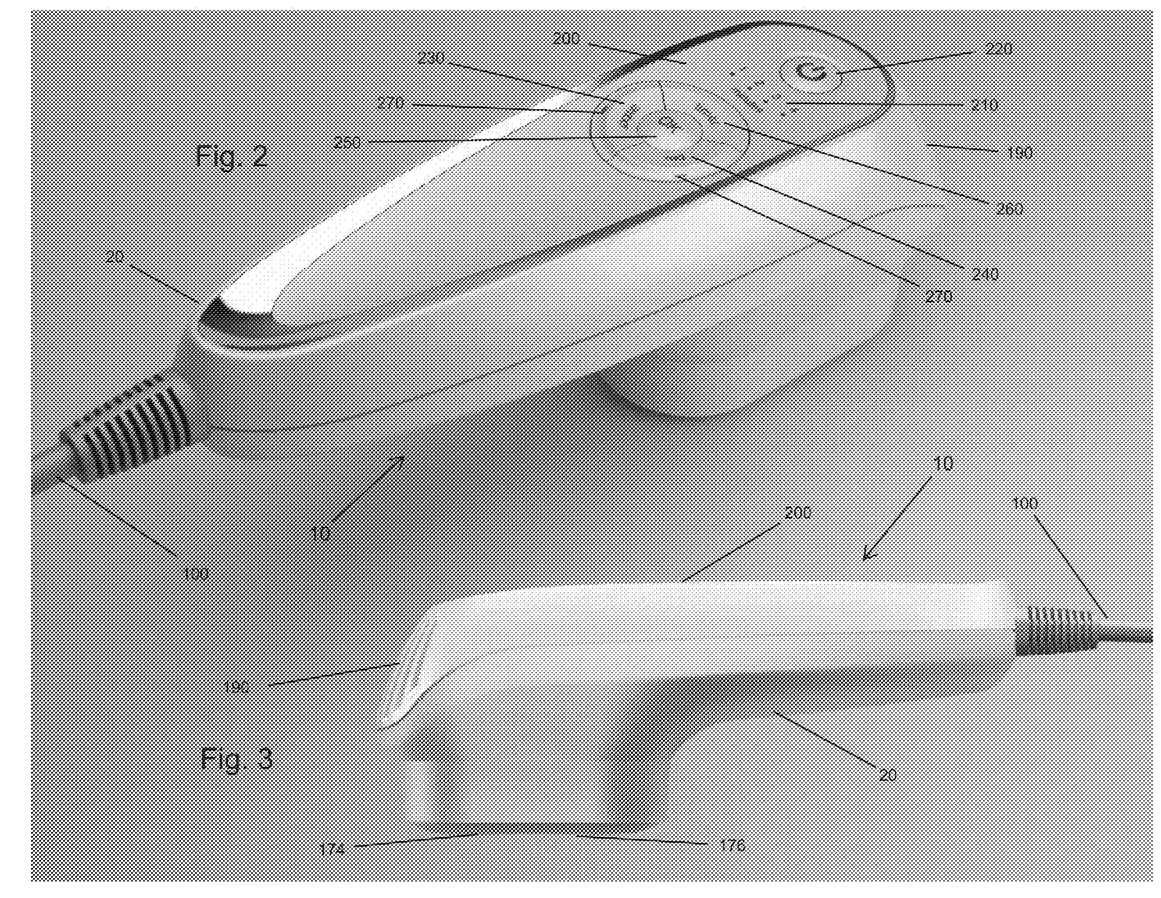
FIG. 2 is a perspective view of a preferred embodiment of the present invention.
FIG. 3 is a side view of a preferred embodiment of the present invention in accordance with FIG. 2.

Referring now to FIGS. 2 and 3, power supply 100 is shown as an AC power cord to provide for a corded version of the apparatus 10. Housing 20 is shown as an ergonomic and both tactilely and visually appealing form, emphasizing the handheld size and convenient configuration of the apparatus 10.

The performance of fan 190 is improved through the provision of depicted vents formed in housing 20 adjacent fan 190. User control area 200 is designed with a layout and configuration that is practical, easy to clean and easy to use. User indicators 210 provide the user with information about the device status and control. Power switch 220 enables a user to easily turn the device 10 on and off. Timer switch 260 and OK switch 250 are depicted in convenient and stylish arrangement with first switch 230 and second switch 240. A plurality of indicator lights 270 may be coupled to one or more other controls to improve feedback to a user.

Figure 4:
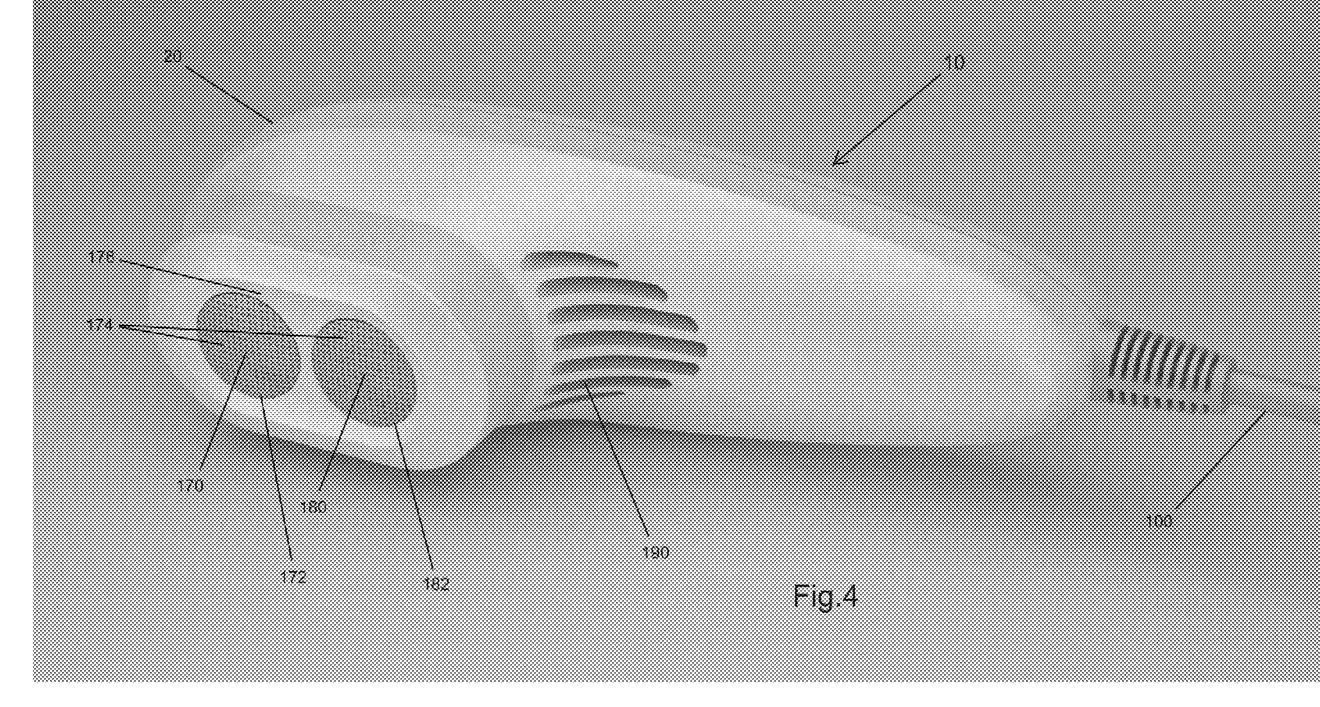
FIG. 4 is a perspective bottom view of a preferred embodiment of the present invention in accordance with FIGS. 2 and 3.

Referring now to FIG. 4, first optic 172 and second optic 182 are shown in cooperative arrangement with the ergonomic and elegantly functional design of housing 20. First LED 170 and second LED 180 are not directly visible in the FIG. 4, but are indicated in their relative position centrally arranged within first optic 172 and second optic 182. Additional optics and associated LEDs are contemplated as being within the scope and breadth of the present invention.

Figure 5A:
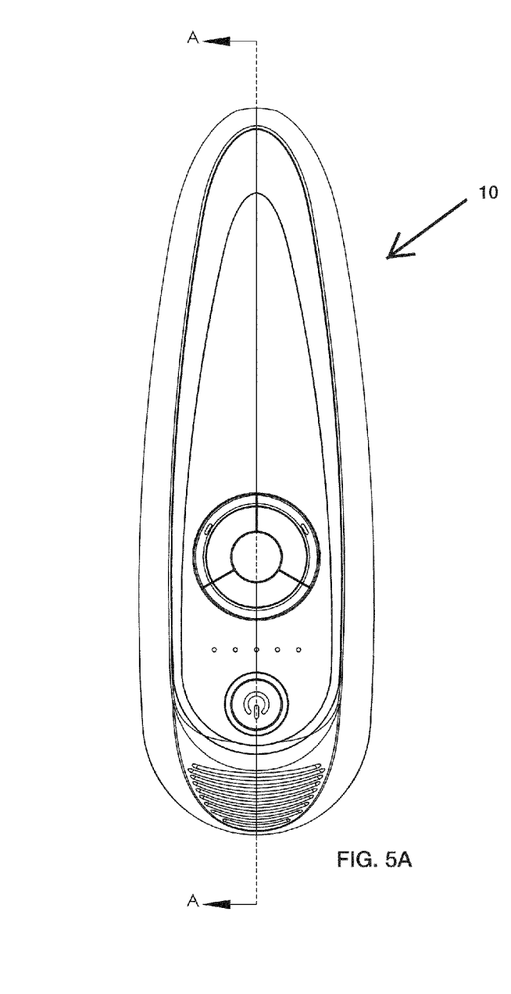
FIG. 5A is a plan view of a preferred embodiment indicating plane A-A.
Figure 5B:
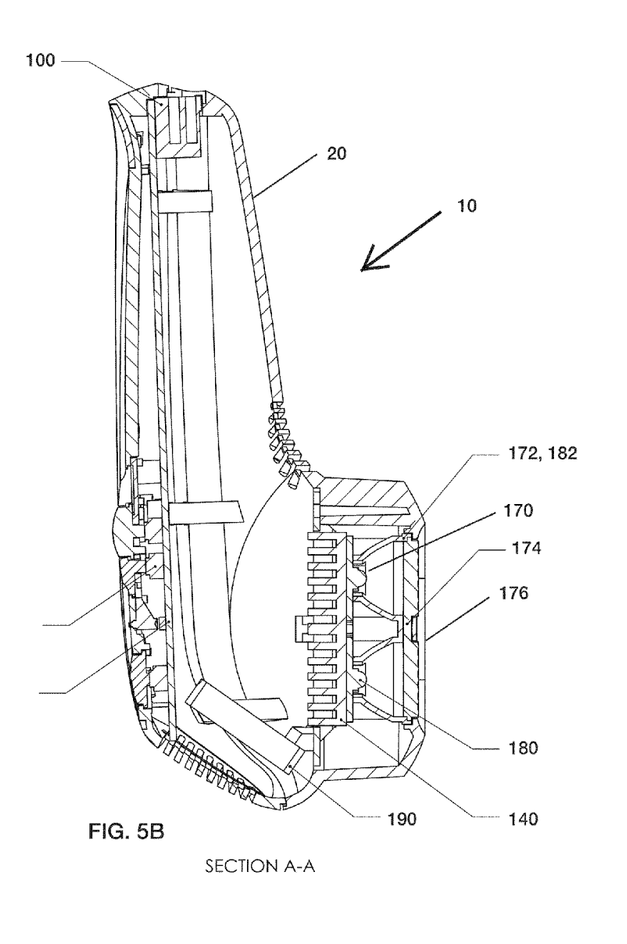
FIG. 5B is a cross-section view along plane A-A as indicated in FIG. 5A.

Referring now to FIG. 5A and FIG. 5B, depicting a plan view and a side sectional view along the A-A plane, respectively. Power supply 100 is shown as a receptacle for a plug-in style connector to an external power source. Such connections are well known to those skilled in the art. Housing 20 is shown in cutaway view to enable viewing of the arrangement of LEDs 170 and 180 with respect to optics 172 and 182, respectively, and diffuser 174. Optical face 176 provides for a sealed surface that is easy to clean and sterilize as needed, and which provides a smooth surface for not unpleasant skin contact when required for treatment. Fan 190 provides necessary cooling of electrical components as needed.

Figure 6:
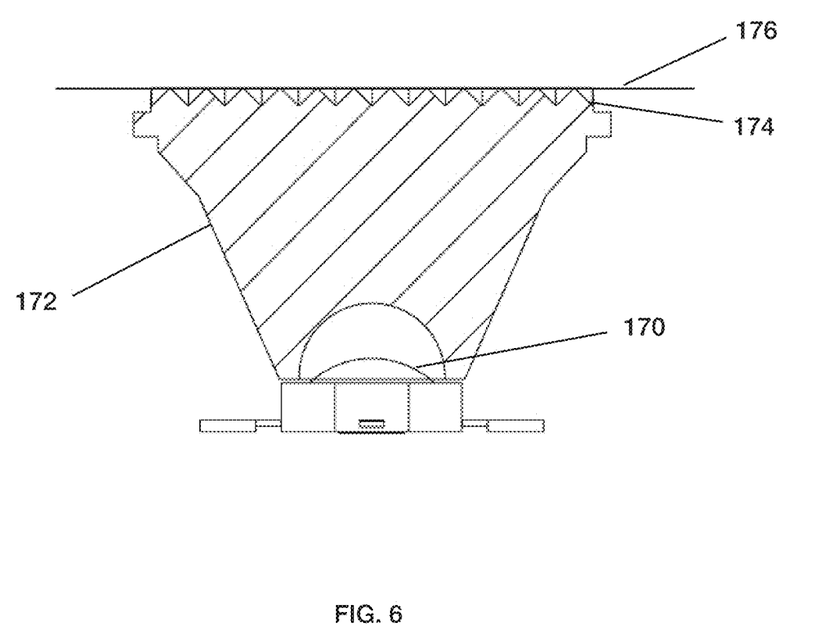
FIG. 6 is a side view of a light emitting diode optic assembly of a preferred embodiment of the present invention.

FIG. 6 shows a side view of a light emitting diode optics assembly in accordance with a preferred embodiment of the present invention. LED 170 is positioned relative to optic 172 for effective collimation and dispersion of generated light energy. Diffuser 174 may be mounted adjacent optic 172 or constructed as an integrated unit, as shown. Diffuser 174 is shown adjacent optical face 176, but may be constructed as an integrated unit if desired.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

In one particular embodiment of the present invention, a device referred to as "Full Wellness" is equipped with a green (525 nm) 3 watt LED with accompanying optic; an amber (590 nm) 3 watt LED with accompanying optic; an near infra-red (850 nm) 3 watt LED with accompanying optic; and, a red (660 nm) 5 watt LED with or without optic.

In another particular embodiment of the present invention, a device referred to as "Mini Wellness" is equipped with a green (525 nm) 1 watt LED with accompanying optic; an amber (590 nm) 1 watt LED with accompanying optic; an near infra-red (850 nm) 1 watt LED with accompanying optic; and, a deep-red (660 nm) 5 watt LED with or without accompanying optic.

In another particular embodiment of the present invention, a device referred to as "Aesthetic Dermatology" is equipped with an amber (590 nm) 3 watt LED with accompanying optic; and a red (660 nm) 5 watt LED with or without accompanying optic.

In another particular embodiment of the present invention, a device referred to as "PhysioMedicine/Pain" is equipped with a deep red (660 nm) 5 watt LED with or without optic; and, an infra-red (850 nm) 3 watt LED with accompanying optic.

In another particular embodiment of the present invention, a device referred to as "Acne Treatment" is equipped with a 415 nm LED and a red (660 nm) LED, each LED being rated from 1 to 10 watts and used with or without accompanying optics.

All wavelengths and/or ranges of wavelengths cited herein are plus or minus 5 nanometers. All optics cited herein provide beam angles of distribution within ranges of plus or minus 5 degrees of the given value/s.

In a series of tests, photobiology devices in accordance with the present invention were used to evaluate effectiveness of treatment for a variety of disorders. All subjects were volunteers, uncompensated for their participation. Application times were limited to from 1 to 5 minutes for total body use and did not exceed two treatment sessions per day. All volunteers wore protective eye goggles similar to those used in UV tanning beds. Volunteers were advised to stay well hydrated after each treatment.

In one application of photobiology treatment employing methods and devices of the present invention, a female subject in her mid-twenties presented complaints of osteo- and rheumatoid arthritis, with primary pain in right hip. Subject required use of crutches to walk. Method of treatment comprised once and twice daily application of device for sessions of 1-5 minutes. Volunteer reported ability to walk without crutches and greatly reduced pain after one treatment. After one week, reported increase in muscle mass, strength and no pain.

In another application of photobiology treatment employing methods and devices of the present invention, a male subject in his mid-sixties presented complaints of chronic knee pain and inability to exercise. Treatment was applied via high-powered LED light from an apparatus in accordance with the present invention. Treatment sessions of one to five minutes each were applied to both knees. Subject reported greater flexibility and reduced pain. Continued use of device and treatment for two weeks produced improved strength and ability to resume exercise.

Treatment methods in accordance with the present invention call for the application of light from the device for a selectable period of time, generally from one to five minutes, with the light directed at and in relatively close proximity (generally, from 1 to 4 inches) to the area for treatment. Such treatment methods also comprise a repetition of applications of device light at a frequency of from one or more times a day.

For treatment of wounds and/or healing of superficially bruised tissue, a high-powered red LED having an emitted light frequency of generally 660 nm is provided as one of LEDs 170 and 180 for the device. By making selection with user control 200, a user selects the high-powered red LED from switches 230 and 240, and selects desired treatment time with timer switch 260. Confirming these settings with OK switch 250 initiates treatment session. The user then places the optical face 176 in proximity to the wound or bruised tissue to be treated. The device 10 is to be oriented with optical face 176 stationary and parallel to the skin surface area to be treated. For wounds and bruised tissue, the optical face 176 is to be positioned within two inches (2") of the treatment area. Treatment duration may vary from 30 seconds to 5 minutes per area and is to be repeated daily as needed.

For treatment of pain and/or superficial muscle strain, a high-powered red LED having an emitted light frequency of generally 660 nm is provided for one of LEDs 170 and 180. As above, a user selects the high-powered red LED and employs a similar treatment with the addition of therapeutic gentle stretching of the tissue/muscle in away from the optical face 176. To treat deeper tissue or strained muscle, a high-powered near infrared LED having an emitted light frequency of generally 850 nm is provided as one of LEDs 170 and 180.

For superficial penetration and myofascial trigger points and relief of neuropathic pain, the red LED output is applied for between 1-5 minutes at a distance of from 2" to contact with the treatment area. Such treatment is repeated from daily to three times per week as needed. For deeper penetration and trigger point stimulation and joint injuries, the near infrared LED output is applied for between 2 to 6 minutes. Such treatment is repeated from daily to three times per week as needed.

For facial toning and/or photo rejuvenation, a high-powered amber LED having an emitted light frequency of generally 590 nm is provided as one of LEDs 170 and 180. The user should smile gently while applying light treatment once every other day for 1 to 5 minutes. Light application should cover the area under the chin, the entire face and top of scalp, and behind the ears. Mouth should be opened during treatment while smiling and light should be applied to inside of mouth and cheek muscles. Direct application of light to thyroid gland should be avoided. To stimulate acupuncture or trigger points, light from the amber LED should be applied to selected points once a day for a time period of from 30 seconds to 3 minutes. Total time of light application should not exceed 5 minutes.

It is apparent from these examples that the photobiology device 10 of the present invention produces a variety of specific light energy wavelengths for the treatment of a number of medical conditions.

Similar treatments with the device of the present invention, and similarly remarkable results have been achieved for patients suffering from knee injuries, osteoarthritis, chronic pain, anxiety, muscle tone, sciatica, bursitis, mouth sores, lower back pain, hip and leg pain, athlete's foot, carpal tunnel syndrome, bladder dysfunction, arthritic pain in hands and feet/ankles, ankle or joint sprain, knee pain, sports injuries, hemorrhoid, warts, cold sores, scoliosis, lower back pain, migraine headache, eczema, shingles, neuropathic pain, hematoma, skin ulcers, psoriasis, and pressure sores.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A portable high-powered light emitting diode photobiology device for use in human and/or animal phototherapy applications and treatments of biological tissues, said device comprising:
    a plurality of light emitting diodes, each of said light emitting diodes having a power rating greater than 1 and less than 10 watts;
    a plurality of optics, each optic comprising a reflector, associated with one of said light emitting diodes and providing dispersion angles of 45-90 degrees, for enhancing light intensity;
    a user control area providing indicators and switches by which a user may select and confirm desired treatment parameters;
    a housing substantially enclosing and retaining said light emitting diodes, optics and user control area;
    an optical face substantially integrated with said housing to provide a smooth surface toward the area of treatment, said optical face comprising a diffuser for improving uniform dispersion of light.

2. The portable photobiology device of claim 1, wherein said plurality of light emitting diodes comprises red diodes, near infrared diodes and amber diodes.

3. The portable photobiology device of claim 1, wherein at least one of said plurality of light emitting diodes comprises a amber diode emitting light at 590 nm.

4. The portable photobiology device of claim 1, wherein at least one of said plurality of light emitting diodes comprises a red diode emitting light at 660 nm.

5. The portable photobiology device of claim 1, wherein at least one of said plurality of light emitting diodes comprises a near infrared diode emitting light at 850 nm.

6. The portable photobiology device of claim 1, wherein at least one of said plurality of light emitting diodes comprises a blue diode emitting light at 415 nm.

7. The portable photobiology device of claim 1, wherein at least one of said plurality of light emitting diodes comprises a green diode emitting light at 525 nm.

8. The portable photobiology device of claim 1, wherein said user control area further comprises indicators to provide a user with device and control status, a power switch, a timer switch for a user to select a desired duration, an OK switch for confirmation of settings, first and second switches for selecting of desired light source, and a plurality of indicator lights.

* * * * *